(12) United States Patent
Iversen et al.

(10) Patent No.: US 6,424,886 B1
(45) Date of Patent: Jul. 23, 2002

(54) PROSTHETIC ARM POWERED BY AN ULTRASONIC MOTOR

(75) Inventors: Edwin K. Iversen; James R. Linder; Harold H. Sears, all of Salt Lake City, UT (US)

(73) Assignee: Motion Control, Inc., Salt Lake City, UT (US)

( * ) Notice: Subject to any disclaimer, the term of this patent is extended or adjusted under 35 U.S.C. 154(b) by 0 days.

(21) Appl. No.: 09/690,241

(22) Filed: Oct. 17, 2000

Related U.S. Application Data

(63) Continuation-in-part of application No. 09/576,398, filed on May 22, 2000.

(51) Int. Cl.[7] .............................................. G05B 19/04
(52) U.S. Cl. ........................ 700/254; 700/213; 700/250; 623/33; 623/34; 623/44; 623/58; 403/90; 403/128; 403/131; 403/321
(58) Field of Search ................................. 700/254, 213, 700/250; 623/33, 38, 44, 34, 53, 27, 36, 39, 24, 58, 63, 57, 43; 403/90, 128, 131, 321

(56) References Cited

U.S. PATENT DOCUMENTS

| | | | | |
|---|---|---|---|---|
| 4,895,574 A | * | 1/1990 | Rosenberg | 623/24 |
| 5,888,213 A | * | 3/1999 | Sears et al. | 623/24 |
| 5,888,237 A | * | 3/1999 | Shiraishi et al. | 623/44 |
| 5,899,943 A | * | 5/1999 | Shiraishi et al. | 623/44 |
| 6,206,932 B1 | * | 3/2001 | Johnson | 623/38 |

OTHER PUBLICATIONS

Scott Chou and Steve Thackery, "Miniature Ultrasonic Motor," Horological Journal Article of the month Feb., 1999, pp. 1–6.

Shyh–Shiuh Lih, Yoseph Bar–Cohen and Willem Grandia, "Rotary Ultrasonic Motors Actuated by Traveling Flexural Wave," Presented at the SPIE International Conference, Smart Structures and Materials Symposium, Enabling Technologies: Smart Structures and Integrated Systems, San Diego, CA 3–6 Mar., 1997.

Yoseph Bar–Cohen, Xiaoqi Bao and Willem Grandia, "Rotary Ultrasonic Motors Actuated by Traveling Flexural Wave," Proceedings of the Smart Structures and Materials Symposium, San Diego, CA 1–5, Mar. 1998, Paper 3329–82.

H. Das, et al., "Robot Manipulator Technologies for Planetary Exploration," Proceedings of the 6th Annual International Symposium on Smart Structures and Materials, Mar. 1–5, 1999, Newport Beach, CA, Paper No. 3668–17.

Xiaoqi Bao and Yoseph Bar–Cohen, "Complete Modeling of Rotary Ultrasonic Motors Actuated by Traveling Flexural Wave," Proceedings of SPIE's 7th Annual International Symposium on Smart Structures and Materials, Mar. 1–5, 2000, Newport, CA, Paper No. 3992–103.

(List continued on next page.)

*Primary Examiner*—William A. Cuchlinski, Jr.
*Assistant Examiner*—Marc McDieunel
(74) *Attorney, Agent, or Firm*—Thorpe North & Western, LLP

(57) ABSTRACT

A movable prosthetic limb includes a drive linkage which is configured to move the prosthetic limb. An ultrasonic drive motor is coupled to the drive linkage and powers the drive linkage. The ultrasonic motor is non-backdrivable and has high torque at low speeds. Specifically, a prosthetic limb uses an ultrasonic motor to drive an elbow joint or prosthetic fingers. A movable prosthetic wrist includes a base configured to be coupled to an amputee. An ultrasonic drive motor is attached to the base, and a hand piece is attached to the ultrasonic drive motor to form a wrist joint. In this configuration, the ultrasonic drive motor directly moves the wrist joint. A harmonic drive can also be used for gear reduction in the wrist joint.

22 Claims, 6 Drawing Sheets

OTHER PUBLICATIONS

Garvin et al, Amputations and limb prostheses, 1999, Iternet, pp. 1–41.*

Morimoto et al., Ultrasonic scanning system for prosthetid applications in rehabililtation medicine, 1993, IEEE, pp. 1354–1356.*

Wolpert et al., Recreating life–like motion in robotic limbs, 1993, IEEE, pp. 116–118.*

Elsey, Adaptive control of prosthetic limbs using neural networks, 1990, pp. 771–776.*

Hudgins et al., The recognition of myoelectric patterns for prosthetic limb control, 1991, IEEE, pp. 2040–22041.*

* cited by examiner

PROSTHETIC ARM POWERED BY AN ULTRASONIC MOTOR

This application is a continuation-in-part of U.S. patent application Ser. No. 09/576,398 filed on May 22, 2000, issued on Jan. 14, 2002.

TECHNICAL FIELD

The present invention relates generally to a mechanical grip device powered by an ultrasonic motor, particularly useful as a prosthetic hand.

BACKGROUND

There are an estimated 100,000 individuals with the loss of arms or hands in the United States alone and as many as 10,000 new amputees each year. Research has been carried out in the area of providing prosthetic limbs for many years. The result of this research has provided complex multiple degrees-of-freedom hands, which are too large and complex to be feasible in the marketplace. In contrast, a number of more commercially viable and affordable one-degree-of-freedom hands have been created. These prosthetic hands are combined with powered prosthetic elbows. The hands and elbows are driven by small electric motors. Command signals to drive the powered motors are provided by electrodes which receive electrical signals from the amputee's remaining muscles.

The practical one-degree-of-freedom prosthetic hands or gripping devices that have become commercially available have a number of shortfalls. One of these problems is the weight of the prosthetic hands. Prosthetic hands on the market, which have a relatively high gripping force, weigh more than 16 ounces. This weight is due, in part, to the weight of the electromagnetic motors and gear reductions used. For hands weighing less than 13 ounces, the strength of the grip is cut in half because the size and strength of the motor. are reduced.

It is a significant problem in a prosthesis to provide a small a high torque motor. This is because the motor must be small enough to fit within the envelope of the amputee's limb that is being replaced. In industrial and scientific robotic applications, torque is increased by increasing the motor size or increasing the electrical power delivered to the motor. This is not possible in prosthetics because an increase in motor size increases the weight of the prosthesis an amputee must constantly carry and it is not aesthetically pleasing. A larger motor results in the motor protruding from the prosthetic limb. Furthermore, increasing the power delivered to the motor is not possible in a prosthesis because the power source must be portable and must remain small. Accordingly, it would be valuable to have a motor for use in a prosthesis which provides a high torque output without increasing the motor size or power requirements.

SUMMARY OF THE INVENTION

It has been recognized that it would be advantageous to develop a system to provide a prosthesis with a mechanical power source which reduces the weight of the prosthesis, runs more quietly, provides a more direct drive, and has low power consumption.

In accordance with one aspect of the present invention, a movable prosthetic limb includes a drive linkage, which is configured to move the prosthetic limb. An ultrasonic drive motor is coupled to the drive linkage and powers the drive linkage. The ultrasonic motor is non-backdrivable and has high torque at low speeds. Specifically, a prosthetic limb can use an ultrasonic motor to drive a prosthetic elbow joint or prosthetic fingers.

In accordance with another aspect of the present invention, a movable prosthetic wrist includes a base configured to be coupled to an amputee. An ultrasonic drive motor is attached to the base, and a hand piece is attached to the ultrasonic drive motor to form a prosthetic wrist joint. In this configuration, the ultrasonic drive motor directly moves the prosthetic wrist joint. A harmonic drive or eccentric gears can also be used for gear reduction in the prosthetic wrist joint.

Another important aspect of the present invention is a prosthetic gripping device having at least two opposable digits. A drive linkage is configured to enable the two opposable digits to grip. An ultrasonic drive motor is used to directly power the drive linkage.

Additional features and advantages of the invention will be set forth in the detailed description which follows, taken in conjunction with the accompanying drawings, which together illustrate by way of example, the features of the invention.

DETAILED DESCRIPTION

Figure 1:
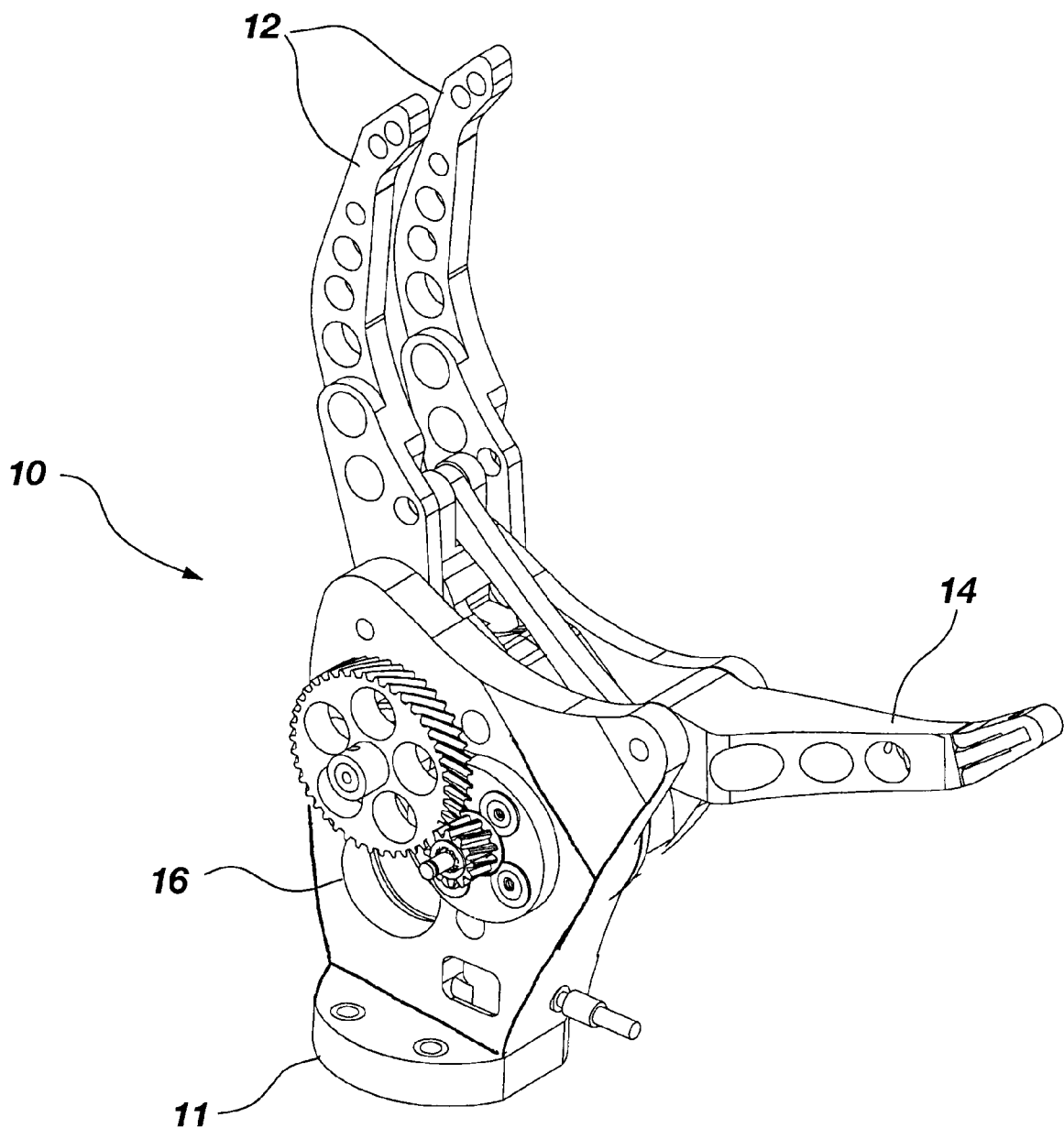
FIG. 1 is a perspective view of a preferred embodiment of a mechanical gripping hand.

For the purposes of promoting an understanding of the invention, reference will now be made to the exemplary embodiments illustrated in the drawings, and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

As illustrated in FIG. 1, a mechanical gripping system 10 is shown for use as a prosthetic hand and for grasping objects. In this description where a hand, wrist, digits or elbow is discussed, this should be assumed to mean a prosthetic hand, wrist, digits or elbow, unless otherwise specifically noted. A gripping device includes at least two opposable digits 12, 14 and a drive linkage inside the grip mechanism. The gripping device is conventionally powered by a drive motor mounted into a space 16 in the grip base 11, and the drive motor enables the two opposable digits to grip. The prior art motor used in a prosthetic limb is an electromagnetic motor. For example, the motor can be a basket wound high torque to inertia motor with heavy duty graphite/copper composite brushes or another conventional heavy duty electromagnetic motor known to those skilled in the art.

A major problem with using electromagnetic motors in prosthetics is the size and the weight they add to the prosthesis. Electromagnetic or other DC electric motors are effective in a prosthetic limb. Unfortunately, the motors are a few inches long and have a relatively large cross-sectional area which takes up a significant amount of space in the prosthetic limb. The windings and metal components used to form the motor also increase the weight of the prosthetic device. This is detrimental because an amputee wears the prosthetic limb for extended periods of time (10 or more hours a day) and every ounce of weight is significant.

Electromagnetic motors also have the disadvantage of a very low movement strength. Only about 0.1 W/cm$^3$ of power are produced in an electromagnetic motor. Hydraulic pressure on the other hand can deliver 20 W/cm$^3$ of power. Hydraulic pressure can provide almost 200 times the power per mass as compared to an electromagnetic motor. Natural muscle provides about 7 times the work per mass as an electromagnetic motor and pneumatic pressure generates about 35 times the work per mass. Of course, hydraulic pressure and pneumatic pressure require large pumps and reservoirs and are not practical for mobile applications. Thus, electromagnetic motors have been exclusively used in mass-produced, mobile prostheses.

In order to capture the torque required to power a prosthetic device with an electromagnetic motor, gear reductions are used to increase the torque. Electromagnetic motors have a high speed and low torque which can be converted to high torque. This requires a number of gears and several gear boxes to reach the desired level of torque for given speeds. For greater speeds and lower torque, less gear reduction is needed. For higher torque and lower speeds a greater gear reduction is used. Using many gears or a few gear boxes increases the weight of the prosthetic device. A gear box also has notable losses from friction and wear. Furthermore, the overall transmission and drive linkage become noisier as the number of gears increases. The noise of a prosthetic device is significant to an amputee. It is important that there is as little noise as possible so they do not attract attention to themselves. Being an amputee is difficult, even without loud mechanical noises being produced from a prosthesis.

Figure 2:
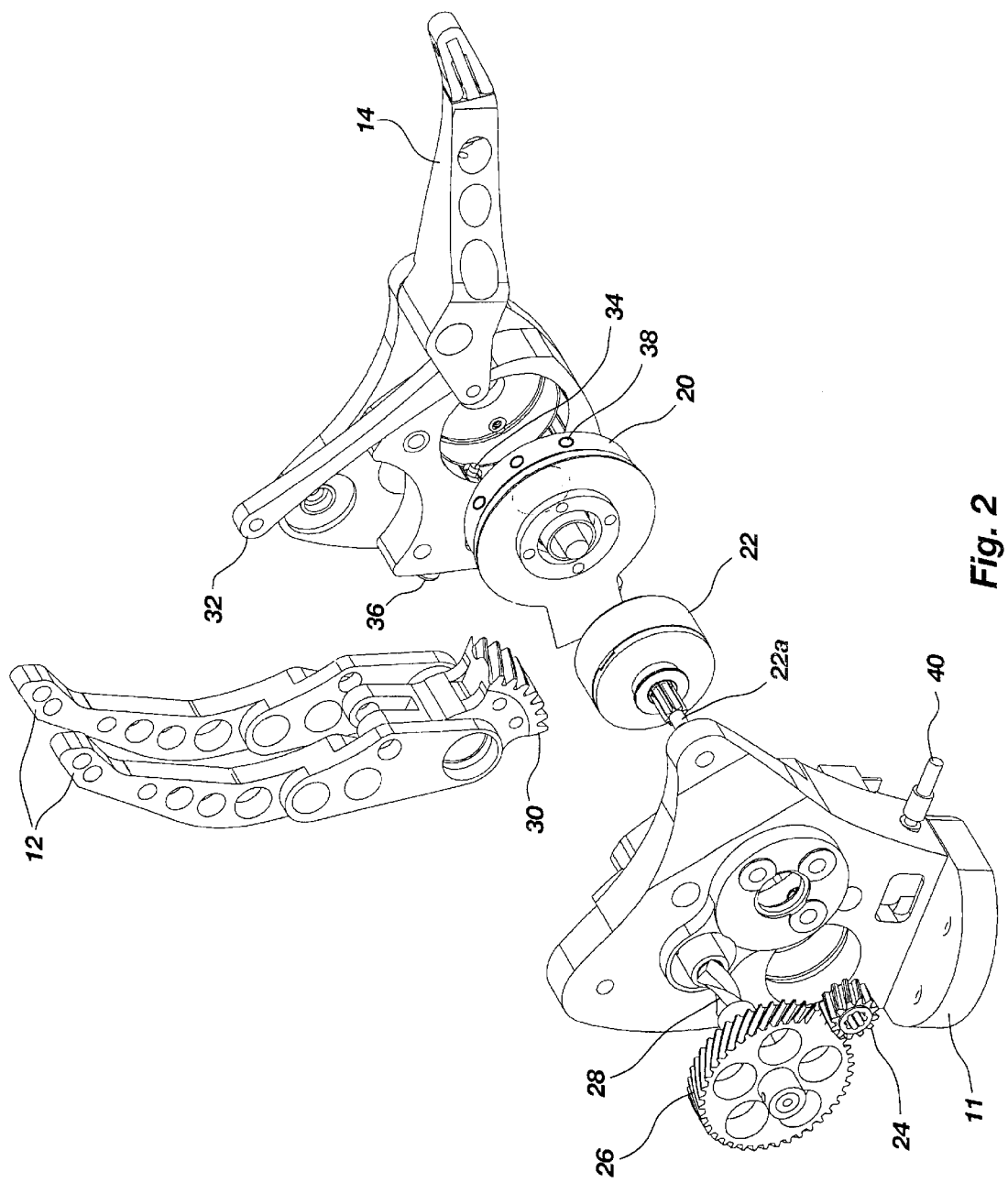
FIG. 2 is an exploded perspective view of a mechanical gripping hand of FIG. 1.

Referring now to the exploded view of the mechanical gripping device as illustrated in FIG. 2, the drive linkage comprises a drive and transmission attached to an ultrasonic drive motor 20. More particularly, the drive linkage includes a number of gear reductions and drive gears to transfer power from the motor to the opposing digits 12, 14. The ultrasonic motor directly drives a two-speed transmission 22 which has a 7:1 reduction ratio in the preferred embodiment. The two-speed transmission shifts the drive down to produce more torque as the load increases. A two-speed transmission allows the hand to have high speed while free running, and strength while grasping an object. The automatic two-speed transmission operates by means of a torque sensing spring which allows the transmission to change gear reductions when the transmission is loaded. A two-speed transmission allows the hand to be both strong and fast.

Alternately, the ultrasonic motor 20 can drive planetary gears, or friction planetary gears can be coupled to the two-speed transmission 22 to provide the additional gear reduction. The two-speed transmission is preferred to a single speed gear reduction because of the need for a high speed with less torque and a low speed with more torque in the prosthetic hand.

The two-speed transmission output 22a drives a pinion gear 24 or output gear, which in turn drives a 44-tooth gear 26. The 44-tooth gear is connected to a 3-tooth gear 28 which drives a sector gear 30 and moves the opposable fingers 12, 14. These gears collectively create an output gear reduction assembly. The opposable fingers are connected by a rod 32 and are simultaneously driven by the same sector gear. It is important to note that the space 16 which would conventionally contain a relatively long electromagnetic motor is empty. This provides a significant weight reduction over previous prosthetic hands.

Figure 3:
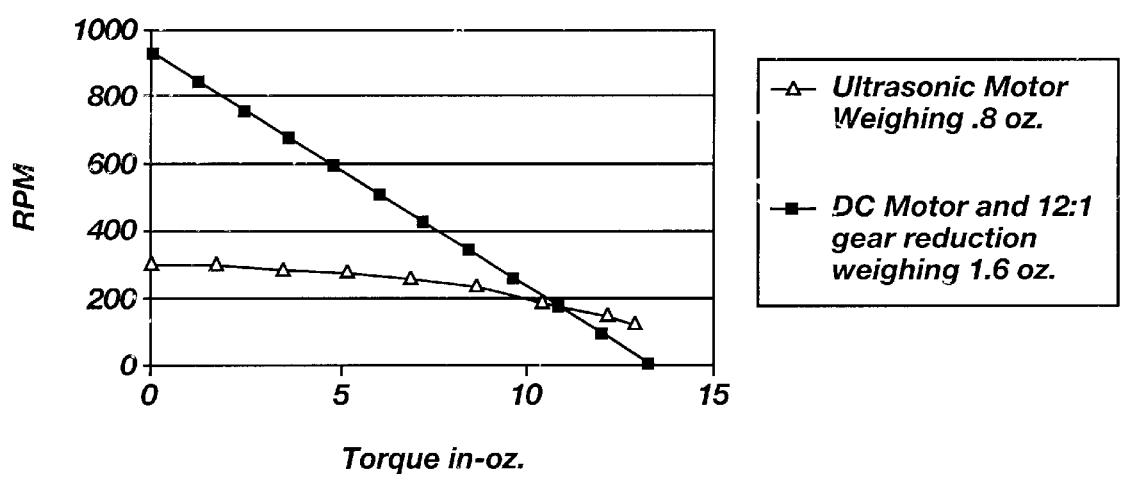
FIG. 3 is a chart depicting the torque of an electromagnetic motor with a gear reduction as compared to an ultrasonic motor without a gear reduction.

FIG. 3 illustrates the torque delivered by an ultrasonic motor without any gear reduction as compared to the torque delivered by an electromagnetic DC motor with a 12:1 gear reduction. The figure illustrates the torque output over a range of 0 to 1000 RPMs (rotations per minute). Prosthetic devices need a high torque with a low motor weight. Without gear reduction, the ultrasonic motor at low RPMs exceeds the torque of the DC motor with a gear reduction. Higher torque is provided even though the ultrasonic motor is half the weight of the DC motor and gear reduction. This is a surprising result and an important advantage for using an ultrasonic motor in a prosthetic hand, wrist, or elbow. The torque to weight ratio of an ultrasonic motor is 10 times higher than an electromagnetic motor. Not only is the weight reduced but a whole gear reduction can be removed. As depicted by the chart, a minimum of a 12:1 ratio gear reduction can be removed (if not more). When gears are driven at 1000–3000 RPM, this produces sounds in the audible range. Removing gears or gear boxes makes the input gears operate at 100–300 RPM. At this lower speed, the noise of the gears and the system is significantly reduced.

Ultrasonic motors have low power requirements which makes them easier to power from a portable battery source. Amputees want to carry as small of a battery as possible. An ultrasonic motor allows the use of a smaller power source than an electromagnetic motor. Lower power requirements can also translate into a longer battery life for the portable battery source.

Another element that is normally present in a prosthetic hand is a backlock. The backlock is a spring-loaded assembly which can be driven in a clockwise or counterclockwise direction from the motor or power supply side of the transmission. Conversely, the backlock cannot be driven from the load or digit side. The backlock is conventionally an important part of the prosthetic hand's drive linkage. When an object is grasped, power cannot be cut to the electromagnetic hand motor without the backlock. A backlock allows the grip to be maintained without power being applied to the motor. This means that the opposable digits remain locked To unless they are being driven by the motor. The backlock works by means of a spring inside a bore that uncoils and locks the backlock when it is back-driven. An ultrasonic motor is not easily back-driven and so the backlock can be removed from the drive linkage or transmission. This is very valuable because it reduces the complexity and cost of the prosthetic hand.

A position feedback circuit can be included with the ultrasonic motor to determine the present position of the motor. Knowing the current orientation of the ultrasonic motor is possible because a digital circuit can determine the position of the prosthetic device using the motor orientation. Using the ultrasonic motor as its own position sensor can protect the ultrasonic motor from being accidentally back-driven. An ultrasonic motor can be damaged if the back-drive force exceeds a certain threshold. The ultrasonic motor can be configured to sense when the ultrasonic motor is being back-driven. A feedback loop can then drive the ultrasonic motor so that power is delivered to the drive linkage which avoids back-driving the ultrasonic motor.

Another embodiment of the ultrasonic drive is to use coupled ultrasonic motors to drive the drive linkage. This type of load sharing arrangement includes two motors which can either run simultaneously or be sequentially engaged. Both motors can be connected to the same drive shaft with one running at higher speed with lower torque and the other one running at a lower speed with a higher torque. When a load is applied, then the low speed/high torque motor drives the shaft, otherwise the high speed motor takes over. A free wheeling clutch can be used with the low speed motor to make this work. A multiple ultrasonic motor configuration can also use an electrical arrangement to alternately engage the motors as the load is applied.

Returning again to FIG. 2, the ultrasonic motor 20 is fixed in position or grounded relative to the rest of the mechanical gripping system so the drive linkage cannot be back-driven by the load from the opposing digits 12, 14. In this embodiment of the device, the ultrasonic motor is grounded to the base 11 using a spring-loaded safety release pin 34 which locks into the stop holes 38 formed into the ultrasonic motor housing. A safety release assembly 36 is included to release the spring-loaded safety release pin. The safety release assembly can be mounted with MS a fulcrum pin (not shown) or a levered release so a safety release arm can be depressed to remove the safety release pin. The safety release arm is manually depressed by the amputee using their remaining hand (or other prosthetic hand) when there is an emergency and the grip needs to be released.

When the safety release pin 34 is removed from the ultrasonic motor housing, it is able to spin freely and the gear reduction ratios provided by the two-speed transmission or other gear reductions are bypassed. This allows the grip to be released without completely disengaging two of the gears (e.g., the pinion gear from the two-speed transmission) or by putting a very large amount of pressure on the digits to release a slip clutch. The prior art methods of disengaging the gears upsets the delicate balance of the clockwork-like transmission mechanism. The pressure method has the serious drawback that the fingers may not release if the amputee cannot apply enough pressure to the fingers. A rotary electrical connector can be used for the ultrasonic motor so that it can be locked into different positions and still receive electrical power. Slip rings or some other mechanical type of bearings are used to allow the ultrasonic motor to spin freely when it is unlocked. Another configuration does not ground the ultrasonic motor but includes a separate backlock which is grounded in a similar manner.

After the ultrasonic motor housing has been released, no torque can be transmitted in either direction through the transmission. The gears all remain in contact with one another, but they are backdrivable because the ultrasonic motor housing and any gear reductions contained within the housing are released. Only a small amount of gear friction has to be overcome to move the digits passively. Thus, only a few pounds of pressure (e.g., 1–4 pounds of pressure) is needed to open the digits after the safety mechanism is released. When the ultrasonic motor housing is grounded, more than 40 pounds of pressure is required to open the digits. The safety release assembly can also be attached to the on/off shuttle switch 40. Conventionally, this switch controls the power to the mechanical gripping system or prosthetic hand and more specifically the ultrasonic motor 20. When the safety release assembly is connected to the on/off shuttle switch, this allows the amputee to simultaneously shut off the power to the hand and also release the safety release pin 30 by pressing a single switch button 56. Using a single button to combine the two functions eliminates the confusion possible with a two-button configuration. The configuration illustrated in FIG. 2 separates the on/off shuttle switch from the safety release assembly.

Motors in prior art prosthetic limbs have had a radial axis in-line with the radial axis of an actual human arm. When the motor used to power the prosthetic hand or wrist has a radial axis in-line with the radial axis of the actual arm, the hand structure cannot be shortened significantly. The present device rotates the radial axis of the ultrasonic motor so it is normal or 90 degrees to the radial axis of the amputee's actual arm axis. Using the ultrasonic motor in a transverse position contributes to the length reduction of the hand. The shortening of the drive mechanism in the hand allows both a wrist member and the ultrasonic motor driving the opposable digits to fit within the space of an actual adult hand. Moreover, a belt/pulley system or gear coupling is not needed as used in a conventional prosthesis and this is quieter. The direct drive ultrasonic motor removes the gear box that would normally be situated where the ultrasonic motor 20 is shown in FIG. 2. Because there are fewer gears this reduces noise and reduces the hand weight.

Another disadvantage of conventional mechanical grips or prosthetic hands is that the length of the prosthetic hand does not allow a wrist to be incorporated while maintaining a hand length equal to that of an actual adult hand. For example, one prosthetic hand or gripping device manufactured by Otto Bock of Duderstadt, Germany, incorporates a passive wrist by lengthening its prosthetic arm so the arm is longer than a normal human arm. The internal structure of a prosthetic hand must be shortened by about 0.75 inches to integrate a passive unpowered wrist into the hand and still maintain a hand length equal to that of an actual adult hand. The use of conventional electromagnetic motors makes a powered wrist impractical because an additional motor must be added to power the wrist. Even if the motor were added, there would not be space within the envelope of a person's actual wrist to provide the appropriate cosmetic appearance.

Figure 4:
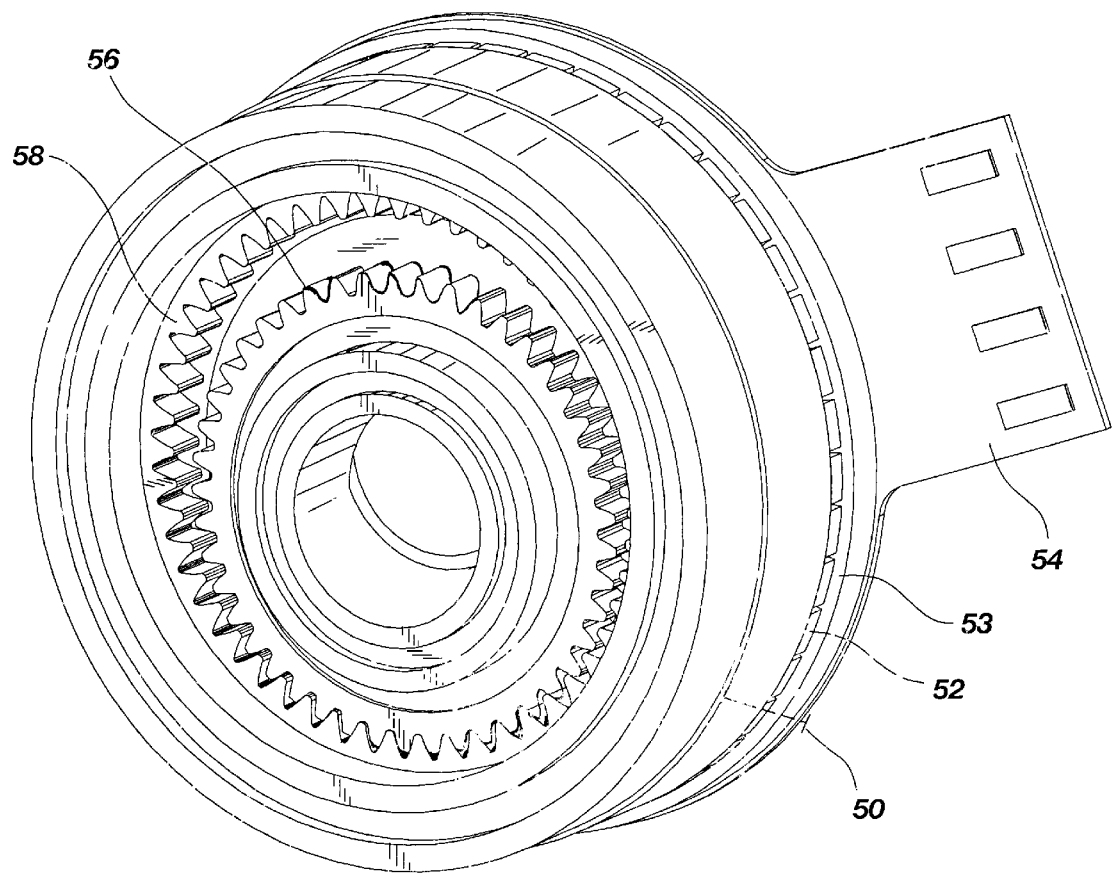
FIG. 4 illustrates a harmonic drive coupled to an ultrasonic motor used in a prosthetic wrist.

FIG. 4 illustrates an ultrasonic motor 50 coupled to a harmonic drive to move a wrist in a prosthetic arm. The comb-like structure 52 is oscillated by piezoelectric crystals 53 which are underneath the combs. Alternatively, the combs themselves can be piezoelectric crystals which are driven at ultrasonic frequencies. An electrode 54 is used to provide the high frequency ultrasonic signals to the motor. A harmonic drive is mounted on top of the ultrasonic motor to drive the hand piece connected to the gear. The harmonic drive comprises an eccentric gear 56 to that rotates within a ring gear 58, and provides a gear reduction in the wrist. Using an ultrasonic motor this way creates a powered wrist within a short amount of space. More than one eccentric gear can also be used to gear down the power from the ultrasonic drive. Alternately, the ultrasonic motor can directly drive the hand piece connected to it.

Using an ultrasonic motor in a prosthetic wrist has significant advantages. Previously in the prior art, a powered wrist was not able to be produced within the envelope of an average human wrist. An electromagnetic motor with the required power is two to three inches in length, and so the prior art increased the length of the arm to accommodate a powered wrist. The present invention uses the ultrasonic motor within the wrist and allows the complete system to fit within the envelope of an actual human wrist.

The ultrasonic motor also has the advantage that it can be ring-shaped to allow electrical connections and control wires for the hand piece to pass through the open center of the ultrasonic motor. Not only does a ring-shaped ultrasonic motor allow for a powered wrist in minimal space, but the control and electrical connections for the hand are not obstructed. This is important because of the value. of keeping all of the prosthetic components within a very compact space. Previously, it has not been recognized that using a ring-shaped motor would help keep the arm components more compact with a powered wrist.

Figure 5:
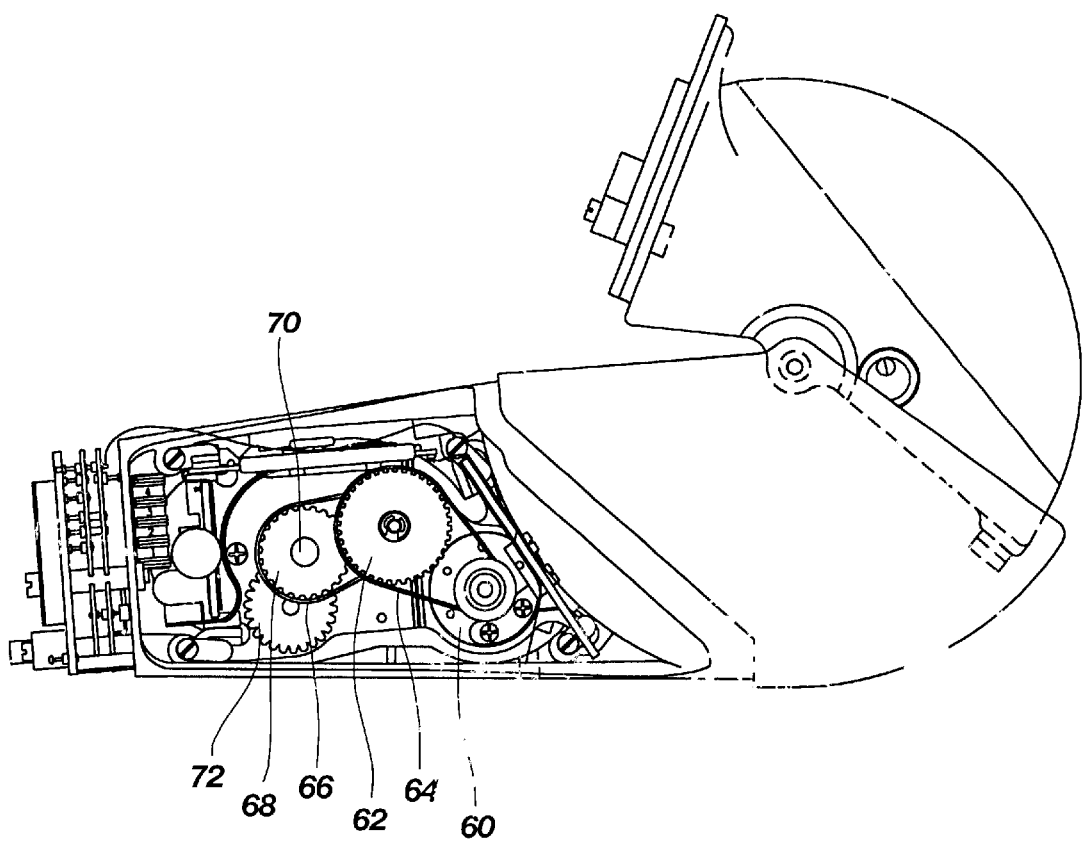
FIG. 5 illustrates a left side view of a prosthetic arm with an ultrasonic motor.

FIG. 5 illustrates a left side view of a prosthetic arm with an ultrasonic motor. Muscle signals from an amputee are amplified and processed by circuitry contained in the arm. These signals activate the ultrasonic motor 60 which drives the movement of the arm. The ultrasonic motor is connected to a first gear 62 by a first pulley 64 which in turn drives a second pulley 66 by and second gear 68. The second gear includes a 2-toothed gear underneath it which drives the 28-tooth gear 72. A 3-tooth gear is underneath the 28-toothed gear and they are connected by the same shaft.

Figure 6:
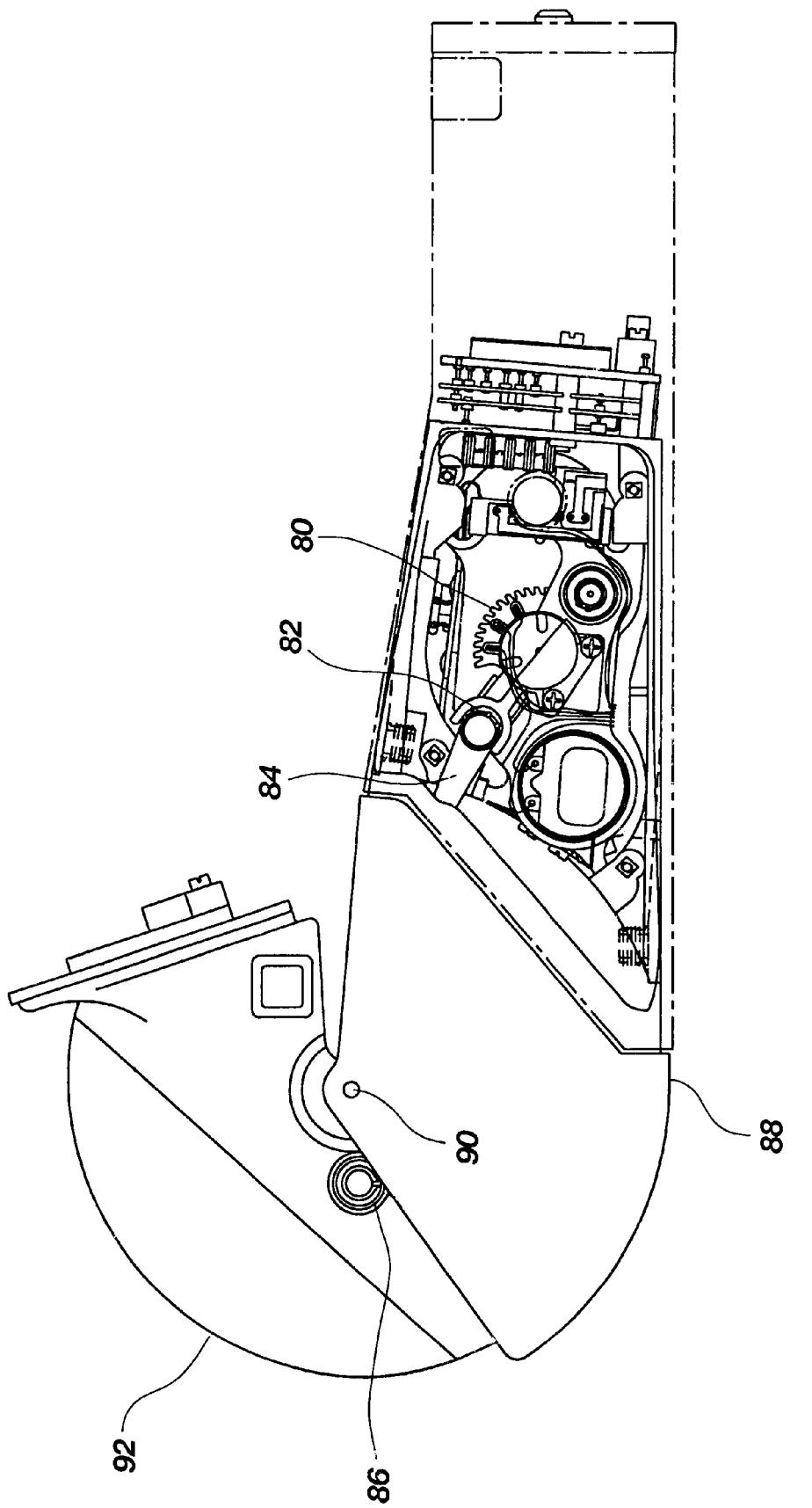
FIG. 6 illustrates a right side view of a prosthetic arm with an ultrasonic motor.

FIG. 6 illustrates a right side view of a prosthetic arm with an ultrasonic motor. The 3-tooth gear (not shown) drives the sector gear 80. The sector gear is connected with a joint 82 to a link arm 84 which is then connected to a load cell 86. The link arm drives the forearm 88 around the elbow hinge pin 90. The load cell detects when a load is placed on the arm so the motor can be driven to match the load. The battery 92 used to power the arm is located in the upper arm or base of the arm. The base of the arm is connected to the amputee.

An important advantage of using an ultrasonic motor to drive the elbow joint is that the high torque per mass of the ultrasonic motor allows the first and second pulleys 64, 66 and their associated gear reductions to be removed. This reduces the weight of the arm and allows the arm to run more quietly. Even though pulleys are more quiet than a gear drive, they do produce noise at high speeds. Using an ultrasonic motor in an elbow also produces the same additional advantages described for the hand and wrist.

A microprocessor controller is also included in the hand for several functions which are listed below.

A) The controller includes automatic adjustment of control parameters to the amputee's EMG signals and uses these signals to control proportionally the speed and grip force of the hand.

B) The controller limits the force of the prosthesis.

C) The power to the hand is shut off when the hand is inactive.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications, including, but not limited to, variations in size, materials, shape, form, function and manner of operation, assembly and use may be made, without departing from the principles and concepts of the invention as set forth in the claims.

What is claimed is:

1. A movable prosthetic limb, comprising:
   (a) a drive linkage, configured to move the prosthetic limb; and
   (b) an ultrasonic drive motor, coupled to the drive linkage, configured to power the drive linkage, wherein the ultrasonic motor is non-backdrivable and has high torque at low speeds.

2. A movable prosthetic limb in accordance with claim 1, further comprising:
   a base, configured to be coupled to an amputee;
   a distal limb piece attached to the base to form a joint, wherein the ultrasonic drive motor drives the drive linkage and moves the joint.

3. A movable prosthetic limb in accordance with claim 1, wherein the joint is an elbow.

4. A movable prosthetic limb in accordance with claim 1, further comprising a pulley to connect the ultrasonic drive motor to the drive linkage.

5. A movable prosthetic wrist, comprising:
   (a) a base configured to be coupled to an amputee;
   (b) an ultrasonic drive motor, attached to the base;
   (c) an ultrasonic drive motor, coupled to the drive linkage, configured to power the drive linkage, wherein the ultrasonic motor is non-bacddrivable and has high torque at low speeds; and
   (d) a hand piece attached to the ultrasonic drive motor to form a wrist joint, wherein the ultrasonic drive motor moves the wrist joint.

6. A movable prosthetic limb as in claim 5, wherein ultrasonic drive motor further includes first and second flat surfaces joined by a rounded edge, and the ultrasonic motor attached to the base at the first flat surface.

7. A movable prosthetic limb as in claim 6, further comprising at least one harmonic gear between the hand piece and. the ultrasonic motor to provide a gear reduction.

8. A movable prosthetic limb as in claim 5, wherein the second flat surface of the ultrasonic drive motor is coupled to the hand piece and directly drives the hand piece rotation relative to the base.

9. A movable prosthetic limb as in claim 5, wherein the ultrasonic motor is ring-shaped to allow electrical connections for the hand piece to pass through the ultrasonic motor.

10. A gripping device having at least two opposable digits, comprising:
    (a) a drive linkage, configured to enable the two opposable digits to grip; and
    (b) an ultrasonic motor to power the drive linkage;
    (c) an ultrasonic drive motor, coupled to the drive linkage, configured to power the drive linkage, wherein the ultrasonic motor is non-backdrivable and has high torque at low speeds.

11. A gripping device in accordance with claim 10, wherein the ultrasonic motor is driven by electrical pulses at ultrasonic frequencies and has high torque at low speeds.

12. A gripping device in accordance with claim 10, wherein the ultrasonic motor is non-backdrivable, which allows the two opposable digits to remain stationary unless driven by the ultrasonic motor.

13. A gripping device in accordance with claim 10, further comprising a pulley to connect the ultrasonic motor to the drive linkage.

14. A gripping device in accordance with claim 10, further comprising a two-speed transmission, coupled to the ultrasonic motor, configured to allow the hand to have high speed and low torque while free running, and high torque when loaded.

15. A gripping device in accordance with claim 10, wherein a plurality of ultrasonic motors are coupled together to power the drive linkage.

16. A gripping device in accordance with claim 15, wherein the plurality of ultrasonic motors are sequentially activated to power the drive linkage.

17. A gripping device in a prosthetic hand having at least two opposable digits and a drive linkage configured to enable the two opposable digits to grip, the drive linkage comprising:
   (a) an ultrasonic motor, having a motor housing with a plurality of stop holes formed therein;
   (b) a drive transmission coupled to the ultrasonic motor;
   (c) a spring-loaded pin, releasably mounted adjacent to the ultrasonic motor, configured to lock into the stop holes; and
   (c) a pin release fastened to the spring-loaded pin, wherein the spring-loaded pin is released from at least one locking hole when the pin release is triggered.

18. A gripping device in accordance with claim 17, further comprising a levered pin release fastened to the spring-loaded pin, wherein the spring-loaded pin is pulled out of at least one stop hole when the levered release is pressed.

19. A gripping device in accordance with claim 17, further comprising a backlock coupled to the drive transmission.

20. A gripping device in accordance with claim 17, further comprising a two-speed transmission coupled to ultrasonic motor, wherein the two-speed transmission provides greater speed under a reduced load and lower speed under an increased load.

21. A gripping device in accordance with claim 20, further comprising:
   (a) an output gear reduction assembly connected to the two-speed transmission;
   (b) a sector gear, coupled to the output gear reduction assembly, configured to drive the opposable digits of the prosthetic hand.

22. A gripping device as in claim 21 wherein the output gear reduction assembly further comprises a three toothed gear wherein the sector gear is driven by the three toothed gear.

* * * * *